United States Patent [19]
Kajii

[11] 3,992,102
[45] Nov. 16, 1976

[54] PHOTOELECTRIC SMOKE DETECTOR WITH MEANS FOR ADJUSTING THE AMOUNT OF LIGHT PROJECTED INTO THE DETECTION REGION

[75] Inventor: Shigeru Kajii, Kawasaki, Japan

[73] Assignee: Hochiki Corporation, Tokyo, Japan

[22] Filed: Apr. 11, 1975

[21] Appl. No.: 567,173

[30] Foreign Application Priority Data
Apr. 17, 1974 Japan.......................... 49-42210[U]

[52] U.S. Cl............................... 356/103; 250/574; 340/237 S; 356/107
[51] Int. Cl.²....................................... G01N 21/00
[58] Field of Search................... 356/103, 104, 207; 250/574; 350/266; 340/237 S

[56] References Cited
UNITED STATES PATENTS

| | | | |
|---|---|---|---|
| 3,240,109 | 3/1966 | Grant, Jr. | 356/207 |
| 3,710,365 | 1/1973 | Barnes | 350/574 |
| 3,723,747 | 3/1973 | Steele | 356/207 |
| 3,868,184 | 2/1975 | Marsocci | 356/103 |

*Primary Examiner*—Vincent P. McGraw
*Attorney, Agent, or Firm*—Haseltine, Lake & Waters

[57] ABSTRACT

In a photoelectric smoke detector of the type wherein the quantity of light incident upon a light receiving element from a light source is varied in accordance with the concentration of the smoke to be detected thereby producing an electric signal, there are provided a light shielding member for preventing the light from the light source from impinging directly upon the light receiving element and an adjusting screw located near top of the light shielding member for adjusting the quantity of the light projecting to the detection region from the light source and the quantity of the reflected light impinging upon the light receiving element from the smoke.

4 Claims, 8 Drawing Figures

PHOTOELECTRIC SMOKE DETECTOR WITH MEANS FOR ADJUSTING THE AMOUNT OF LIGHT PROJECTED INTO THE DETECTION REGION

BACKGROUND OF THE INVENTION

This invention relates to a photoelectric smoke detector and more particularly to a spot type photoelectric smoke detector of the reflected light type.

Photoelectric smoke detectors are classified into two types, that is a direct incident light type or light transmission type which detects the variation in the quantity of the light received by the detector which is caused by the interception of the light from a light source by the smoke to be detected and a reflected light type in which the light emanated from a light source and reflected by the smoke to be detected is detected by a light receiving element. Of these two types, the former is not used as spot type smoke detector because the variation in the quantity of light between normal condition and emergency is small and the S/N ratio of the detector is poor. Although such disadvantages can be alleviated by making long the light path it is difficult to adopt this solution for the spot type detector which is designed to be installed in a limited space. Usually a pulsed lighting system is used for the light source because with the pulsed lighting system it is possible to pass a large current through the light source without increasing power consumption. In the light transmittion type it is necessary to synchronize the operation of the light source and the light receiving element. In the reflected light type such synchronization is also used but is not always necessary.

In the reflected light type it is necessary to preadjust the quantity of the light incident upon the light receiving element so as to suitably bias the photoelectric converting characteristic of the light receiving element by the light emanated from the light source and reflected by the walls or the like where there is no smoke in a space to be supervised. Such adjustment is one of the important factors that determine sensitivity of the detector.

The factors that determine the sensitivity and S/N ratio of the photoelectric smoke detector of the reflected light type are the quantity of the light from the light source and the quantity of light received by the light receiving element and it is desirable to use an adjusting mechanism capable of adjusting these two factors in an interlocked relationship. One solution involves the provision of independent light quantity adjusting means for the light source and the light receiving element but such solution requires two adjusting members thus complicating not only the construction of the mechanism but also the operation thereof. For this reason, in most of the prior art photoelectric smoke detectors of the reflected light type the sensitivity of the detector has been adjusted only by varying the bias voltage of the electric circuit as stated in U.S. Pat. No. 3185975, for example. However, the adjustment of the sensitivity by the adjustment of the electric circuit requires complicated and delicate skills so that more simple and more accurate adjusting means has long been desired in the art.

SUMMARY OF THE INVENTION

Accordingly, it is an object of this invention to provide an improved photoelectric smoke detector capable of adjusting the sensitivity and the S/N ratio of the detector by single adjusting means.

Another object of this invention is to provide a novel photoelectric smoke detector provided with an adjusting mechanism wherein the locking of the adjusting member which is applied for the purpose of preventing an inadvertent movement thereof after it has been set to a desired position can be readily released when it is desired to readjust the adjusting member.

According to this invention these and further objects can be accomplished by providing a photoelectric smoke detector of the type comprising a housing provided with an opening for admitting smoke thereinto, a light source and a light receiving element contained in the housing whereby when the smoke enters into a detection region in the housing the quantity of the light emanated from the light source and impinging upon the light receiving element is varied to produce an electric signal, characterized in that there are provided a light shielding member located in the detection region for preventing the light from the light source from impinging directly upon the light receiving element, and an adjusting screw provided near top of the light shielding member for adjusting the quantity of the light projected into the detection region and the quantity of light impinging upon the light receiving element.

BRIEF DESCRIPTION OF THE DRAWINGS

Further objects and advantages of the invention can be more fully understood from the following detailed description taken in conjunction with the accompanying drawings in which.

DESCRIPTION OF THE PREFERRED EMBODIMENTS

Figure 1:
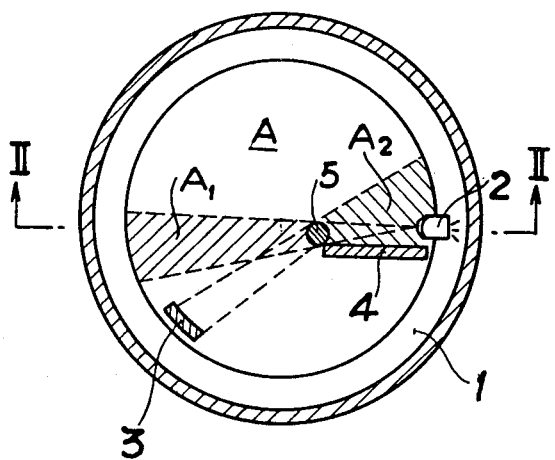
FIG. 1 is a sectional plan view showing one embodiment of a photoelectric smoke detector embodying the invention.
Figure 5:
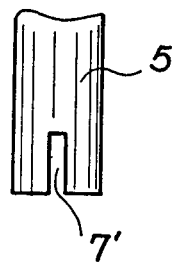
FIGS. 5 and 6 are side views of the lower ends of the adjusting screws showing different constructions for receiving adjusting tools.
Figure 2:
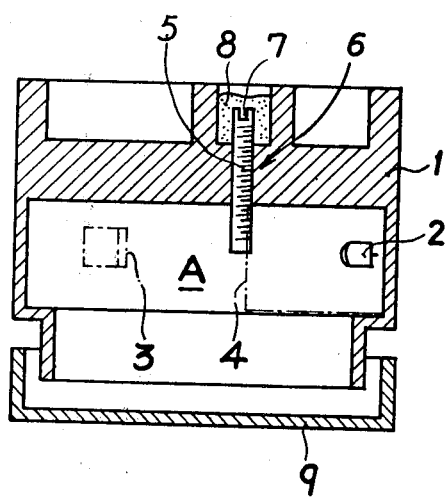
FIG. 2 is a sectional view of the detector shown in FIG. 1 taken along a line II—II.
Figure 6:
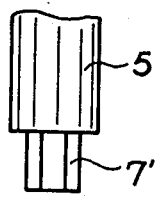

A preferred embodiment of a photoelectric smoke detector shown in FIGS. 1 and 2 comprises a cylindrical housing 1, a light source 2 and a light receiving element 3 which are contained in the housing with thin optical axes intersected at a predetermined angle. A light shielding plate 4 is secured to the housing between the light source 2 and the light receiving element 3 such that the light from the source does not impinge directly upon the light receiving element and near the inner top of the light shielding plate 4 is mounted an adjusting screw 5 to be adjustable in the vertical direction. Thus, a region above a line interconnecting the light source 2, the inner top of the light shielding plate 4 and the light receiving element 3 comprises a detection region A and the smoke entering into this region is detected by the variation in the quantity of the light received by the light receiving element which is caused by the reflection of the light from the light source by the smoke for producing an electric signal.

In the photoelectric smoke detector described above the light shielding plate 4 is provided for the purpose of preventing the light from the light source 2 from directly impinging upon the light receiving element 3 when no smoke enters into the detection region A. Actually, however due to the limits on the fabrication and the machining of the component parts, it is impossible to completely intercept the directly impinging light so that there is a small amount of leaking light. Further, as it is impossible to make the wall surfaces, etc. in the detection region to be perfect black bodies there is a small amount of light reflected by the wall surfaces, etc. Neglecting these background reflected lights, even a slight change in the position of the light shielding plate 4 would cause a large influence upon the detection characteristic or sensitivity of the detector toward smoke. Accordingly, it is desirable to provide means for compensating for the detection error due to slight variation in the position of the light shielding plate which is caused by inaccurate assembling or machining of the light shielding plate.

According to this invention an adjusting screw is provided for this purpose. The adjusting screw 5 shown in FIG. 2 has a groove 7 at its upper end for receiving a screw driver and is threaded into female screw threads 6 provided for a horizontal shelf of the housing 1 for vertical movement. As shown in FIGS. 1 and 2, the adjusting screw 5 is provided near the inner top of the light shielding plate 4 and the lower end of the adjusting screw 5 projects into the detection region A by a desired length. Consequently the adjusting screw provides a fine adjustment of the position of the inner top of the light shielding plate so that it is possible to adjust the quantity of the light projected into a region $A_1$ to the rear of the adjusting screw 5 and also to finely adjust the quantity of light impinging upon the light receiving element 3 from region $A_2$ without changing the position of the light shielding plate 4. In this manner, according to this invention, when the adjusting screw 5 is adjusted by a screw driver not shown it is possible to adjust the quantity of the leakage light impinging upon the light receiving element when there is no smoke, that is the biasing voltage of an electric circuit connected to the light receiving element, by adjusting the quantity of the light projected into rear region $A_1$ and to adjust the quantity of light reflected by the smoke and impinging upon the light receiving element by adjusting the light from the region $A_2$, thus adjusting the sensitivity and the S/N ratio of the detector in an interlocked relatonship. As shown in FIG. 2, a cover 9 is removably mounted on the lower end of the housing 1 with an annular gap there between for shielding the detection region A from external light and for defining an inlet opening for the smoke.

It is advantageous to lock the adjusting screw in the adjusted position and to protect it against moisture by applying a sealing agent 8, such as a silicon elastmer about the upper end of the adjusting screw 5 as shown in FIG. 2. This prevents an inadvertent turning of the adjusting screw which is caused by the mounting operation of the detector on a ceiling, for example. Moreover, it is also possible to prevent water leaking from the coiling or dew drops formed by the moisture in the ambient air from reaching the adjusting screw, thereby efficiently preventing erroneous operation of the detector.

Figure 3:
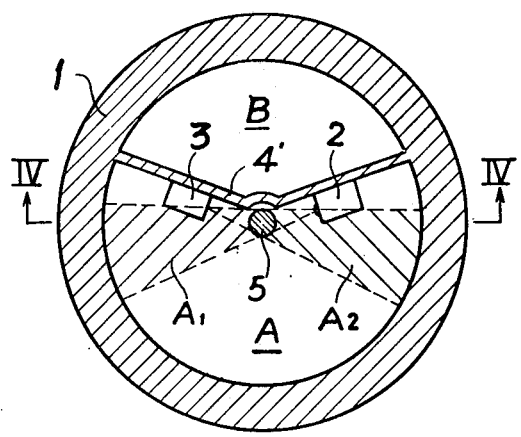
FIG. 3 is a sectional plan view showing a modified embodiment of this invention.
Figure 4:
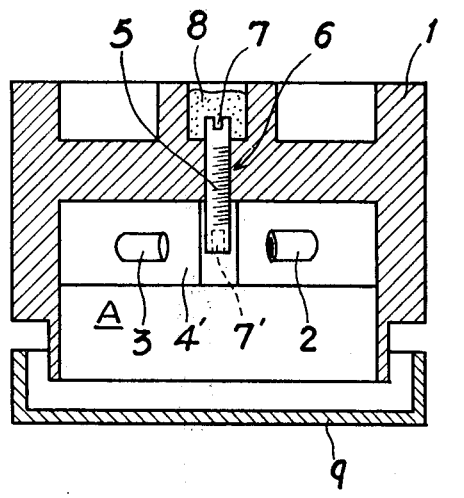
FIG. 4 is a sectional view of the modified detector shown in FIG. 3 taken along a line IV—IV.

In the modified embodiment of this invention shown in FIGS. 3 and 4, the light shielding plate 4 shown in FIGS. 1 and 2 is substituted by a light shielding wall 4′ having a cross-sectional configuration of a sector. In this embodiment, the lower end of the adjusting screw 5 is also provided with a groove or opening 7′ for receiving a screw driver. The construction of the other elements is the same as that of the previous embodiment. In this modification, the light shielding wall 4′ defines a shielded region B having a sector shaped cross-sectional configuration and functions to prevent the light from the light source 2 from directly impinging upon the light receiving element 3 when there is no smoke in the detection region A. It should be understood that the wall 4′ may be a solid block having a volume that fills the region B.

In this modification, the adjusting screw 5 is positioned near the top of the center of the light shielding wall 4′ and its lower end protrudes into the detection region A by a desired length so as to finely adjust the position of the center of the wall 4′. Where readjustment of the detector is necessary, it is necessary to remove the sealing agent 8 on the upper end of the adjusting screw. However, as has been pointed out since a slot 7′ is also provided for the lower end of the adjusting screw, by removing the cover 9 it is possible to raise and remove the sealing agent 8 by turning the adjusting screw by a screw driver inserted into the slot 7′. Thus, it is possible to readjust the screw 5 by inserting the screw driver into the slot 7 on the upper end of the adjusting screw 5 after mounting the cover 9 again. Upon completion of the readjustment, the sealing agent is applied again.

Figure 7:
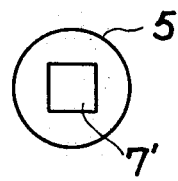
FIGS. 7 and 8 are end views of lower ends of modified adjusting screws.
Figure 8:
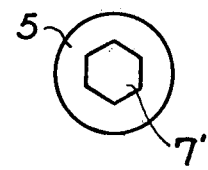

Although the slot 7′ on the lower end of the adjusting screw may be a simple slot for receiving a conventional screw driver but openings having square or hexagonal cross-sectional configuration as shown in FIGS. 7 and 8 are preferred because such openings formed inside of the screw do not change the peripheral profile thereof when it is rotated, thus permitting smooth and linear adjustment of the light quantity. The configuration of the slot 7′ is not limited to those illustrated in FIGS. 5 to 8, but may be eliptical, flat circular or two or more spaced openings or any other configurations that can receive screw drivers, wrenches or other adjusting tools.

Although the electrical circuit connected to the light detecting element has not been shown any well known circuit may be used. For example, as the light source may be used a luminous diode, the intensity of the light produced thereby can be adjusted by varying a resistor connected in series therewith. The output of the circuit is adjusted by adjusting the switching level of the light receiving circuit or by adjusting the output level thereof. Generally the output is adjusted by varying the value of a bias resistor, but it is not only difficult to select a suitable value of th resistor but also the adjustment is stepwise and not smooth and continuous.

What is claimed is:
1. In a photoelectric smoke detector comprising a housing with an opening for admitting smoke thereinto, a light source and a light receiving element contained in said housing whereby when the smoke enters into a detection region in said housing the quantity of the light emanated from said light source and impinged upon said light receiving element is varied to produce an electric signal, the improvement comprising a light shielding member located in said detection region for preventing the light from said light source from impinging directly upon said light receiving element, and an adjusting screw movable along the top edge of said light shielding member for adjusting the quantity of the light projected into said detection region and the quantity of light impinging upon said light receiving element, said light receiving element receiving smoke scattered light from said light source.

2. The photoelectric smoke detector according to claim 1 wherein said adjusting screw is threaded into a threaded opening through said housing and provided with an opening at the upper end thereof for receiving an adjusting tool and wherein the upper end of said adjusting screw is covered by a sealing member for preventing the turning of said adjusting screw and for preventing the moisture in the ambient air from reaching said adjusting screw.

3. The photoelectric smoke detector according to claim 1 which further comprises a cover removally mounted on the lower end of said housing for defining a gap for admitting smoke into the housing between said housing and said cover, the lower end of said adjusting screw being exposed when said cover is removed and wherein the lower end of said adjusting screw is also provided with an opening for receiving an adjusting tool.

4. The photoelectric smoke detector according to claim 3 wherein said opening is formed inside the lower end of said adjusting screw so that the rotation thereof does not change the peripheral profile of said lower end.

* * * * *